United States Patent [19]

Schooley

[11] 4,381,025
[45] Apr. 26, 1983

[54] COVER FOR INSTANT HOT OR COLD PACK

[76] Inventor: Constance E. Schooley, 10443 SW. 120th St., Miami, Fla. 33176

[21] Appl. No.: 333,254

[22] Filed: Dec. 21, 1981

Related U.S. Application Data

[63] Continuation of Ser. No. 260, Jan. 2, 1979, abandoned.

[51] Int. Cl.³ .................... A61F 7/06; B65D 33/16
[52] U.S. Cl. .................... 150/2.4; 224/219; 150/2.6; 128/402; 62/259.3
[58] Field of Search ............ 150/2.4, 2.6, 7, 52 R, 150/52 E, 2.1, 2.2, 2.3; 128/402, 399, 293; 224/219, 222, 228, 224, 235, 236; 62/259.3; 126/271.1, 271.2 C

[56] References Cited

U.S. PATENT DOCUMENTS

| | | | |
|---|---|---|---|
| 858,848 | 7/1907 | Allison | 128/399 X |
| 2,438,643 | 3/1948 | Moore | 128/399 X |
| 2,715,315 | 8/1955 | Giardini | 128/399 X |
| 3,401,695 | 9/1968 | Rosenberg | 150/7 |
| 3,474,781 | 10/1969 | Gaylord, Jr. | 128/293 X |
| 3,510,052 | 5/1970 | Ruda | 150/7 |
| 3,557,853 | 1/1971 | Jones | 150/7 |
| 3,623,485 | 11/1971 | Price | 128/402 |
| 3,815,610 | 6/1974 | Winther | 128/402 X |
| 3,901,225 | 8/1975 | Sconce | 128/402 X |
| 3,916,911 | 11/1975 | Sauder | 62/259.3 |
| 3,943,988 | 3/1976 | Consorti | 150/7 |
| 3,958,750 | 8/1976 | Prybeck | 150/7 |
| 4,044,773 | 8/1977 | Baldwin | 128/402 |
| 4,081,150 | 3/1978 | Tyson | 128/402 |
| 4,092,982 | 6/1978 | Salem | 128/402 X |
| 4,108,351 | 8/1978 | Hough | 150/7 |
| 4,190,183 | 2/1980 | Yates | 224/235 |

FOREIGN PATENT DOCUMENTS 2295885 12/1974 France ...................... 150/7

Primary Examiner—Herbert F. Ross
Attorney, Agent, or Firm—Joseph Zallen

[57] ABSTRACT

A cover for an instant hot or cold pack for use on injured portions of the body where immediate heating or cooling of an affected body part is required. The cover is adapted to be selectively used in either a folded configuration wherein the pack is retained within the cover for placement on the injured area of a large body portion, or in various wrap around configurations wherein the cover can be fastened in surrounding relationship with limbs of various sizes and configurations with the pack retained in intimate contact with the injured area.

7 Claims, 4 Drawing Figures

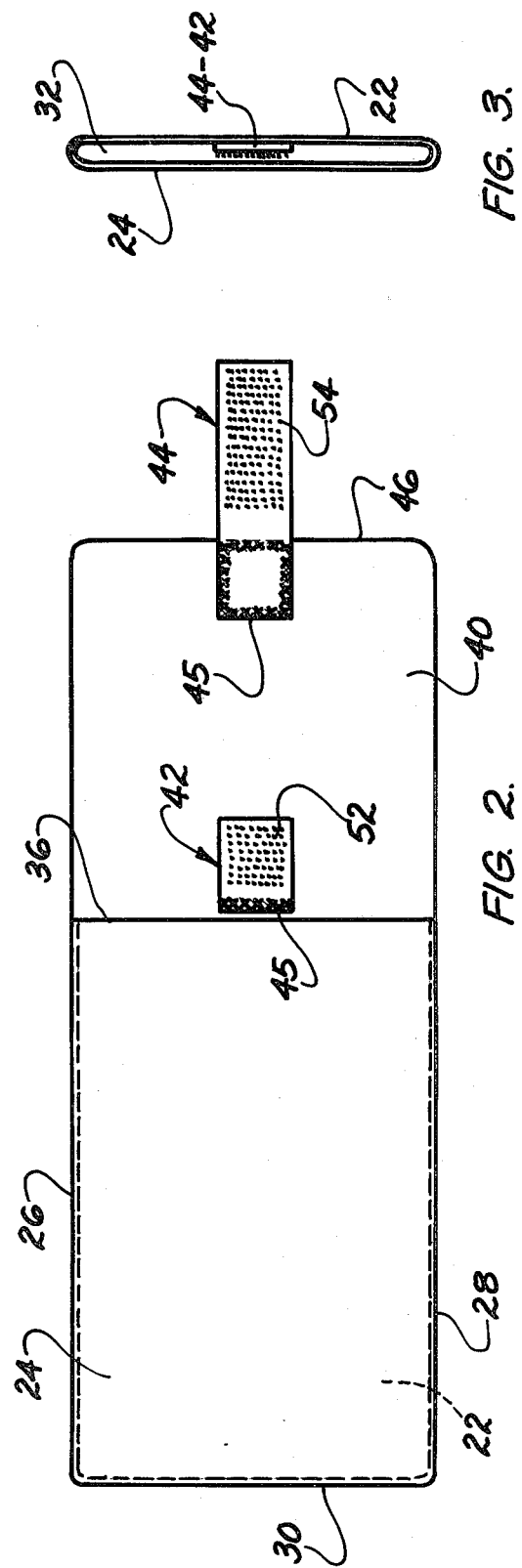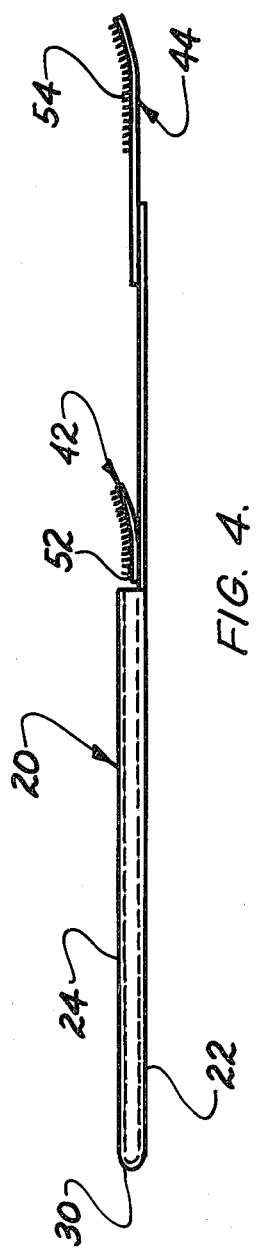

COVER FOR INSTANT HOT OR COLD PACK

This is a continuation of application Ser. No. 260 filed Jan. 2, 1979, now abandoned.

BACKGROUND OF THE INVENTION

This invention relates to packs for application to injured portions of the body, and more particularly to a cover for an instant hot or cold pack adapted for rapid fixation to the injured region during hospital emergency department situations.

PROBLEMS IN THE ART

In the treatment of injuries in Hospitals, it has been one practice in the art to apply localized cooling to injured body portions by the application of compressive wrappings containing a pre-refrigerated gel. This has presented a problem in that a refrigerator must be close at hand to provide the pre-cooled gel, and the compressive force of the wrappings in some instances compounds the damages, and when applied to flexion areas of the body produce swelling of the distal portions.

In the case of emergency department treatment of injuries, it is well known that the optimum time to begin cooling a traumatized area of the body is immediately after the incident occurs. Towards accomplishing this rapid treatment, instant cold packs have been developed which consist of an outer sealed plastic envelope containing ammonium nitrate crystals and a separately packaged solution. When the outer envelope is squeezed, an inner solution package is easily ruptured thereby mixing the contents, whereby the mixture instantly becomes cold. Such instant cold packs are presently being covered with washclothes, both disposable and non-disposable, towels which are not disposable, and other like materials. These attempts to cover the cold packs present problems in that they do not keep the cold application where it belongs, as simple movement of the patient dislodges the device to the stretcher or to the floor.

In such emergency department application of cold packs, the use of complicated multiple wrappings, to secure the pack, presents serious problems, in that rapid fixation is precluded, and since complex wrappings must be made from the distal end of an extremety upwards towards the area of trauma, the patient is subjected to unnecessary moving, increased pain, and the risk of compounding the injury.

In other instances it is desirable to apply heat therapy to regions of the body by using self-heating disposable moist heat packs or pads. Such devices are examplified by a product known as compres which is presently being used by hospitals. In general these devices include heating elements sealed between two layers of soft, flexible polyurethane foam. Heat action is initiated by the immersion of the pad in water, with the heat being felt in one or two minutes and lasting for up to an hour. As in the case of cold packs, these heat pads are presently being wrapped in toweling or the like, and such means of application presents the same problem to the hospital personnel as discussed above in connection with the conventional application of cold packs.

SUMMARY OF THE INVENTION

In general the present invention comprises a novel cover for an instant hot or cold pack, which cover is fabricated from flexible sheet portions of a fabric and pile laminate, so as to be uniquely adapted for use in a variety of applications. The cover with a pack inserted, can selectively be used in a folded configuration wherein the pack is retained in the cover for placement on the injured area of a large body portion, or in various limb encircling configurations wherein the cover can be removably fastened in surrounding relationship with limbs of various sizes and configurations with the pack retained in intimate contact with the injured area.

As another aspect of the present invention the novel cover is adapted for rapid fixation of an instant pack to a traumatized part of the body immediately after an injury occurs, thereby realizing the optimum benefit from the hot or cold application.

As another aspect of the present invention the novel cover provides means for securing an instant pack to an injured limb without complex wrappings and the compressive forces resulting therefrom. This eliminates risk of compounding damage to the effected part, and also prevents induced swelling of distal portions which often results from compressive type wraps.

As another aspect of the present invention, the novel cover provides means for securing an instant pack without movement of the injured body portion which movement would be necessitated in the application of compressive type multiple wrappings.

As another aspect of the present invention the novel cover provides means for instant removal of the pack for easy inspection of affected areas and for replacement of the pack when expired.

As another aspect of the present invention the novel cover is fabricated from a fabric and pile laminate of synthetic resinous material, such as nylon or the like, so as to be water resistant. Hence in the application of cold packs the injured body portion is kept relatively dry, thereby preventing a mode in which bacteria may thrive.

As another aspect of the present invention, the novel cover not only functions as a limb encicling securing means, but also includes an integral pouch provided with a pouch closing fastening means which insures that the pack stays in position without the necessity of applying pressure to fix its location.

Further objects and advantages of the present invention will be apparent from the following description, reference being had to the accompanying drawings wherein a preferred form of embodiment of the invention is clearly shown.

BRIEF DESCRIPTION OF THE DRAWINGS

FIG. 2 is a top plan view of the cover of FIG. 1;

FIG. 3 is an end perspective view of the cover of the preceeding Figures; and

FIG. 4 is a side perspective view of the cover of the preceeding Figures.

DESCRIPTION OF THE PREFERRED EMBODIMENT

Figure 1:
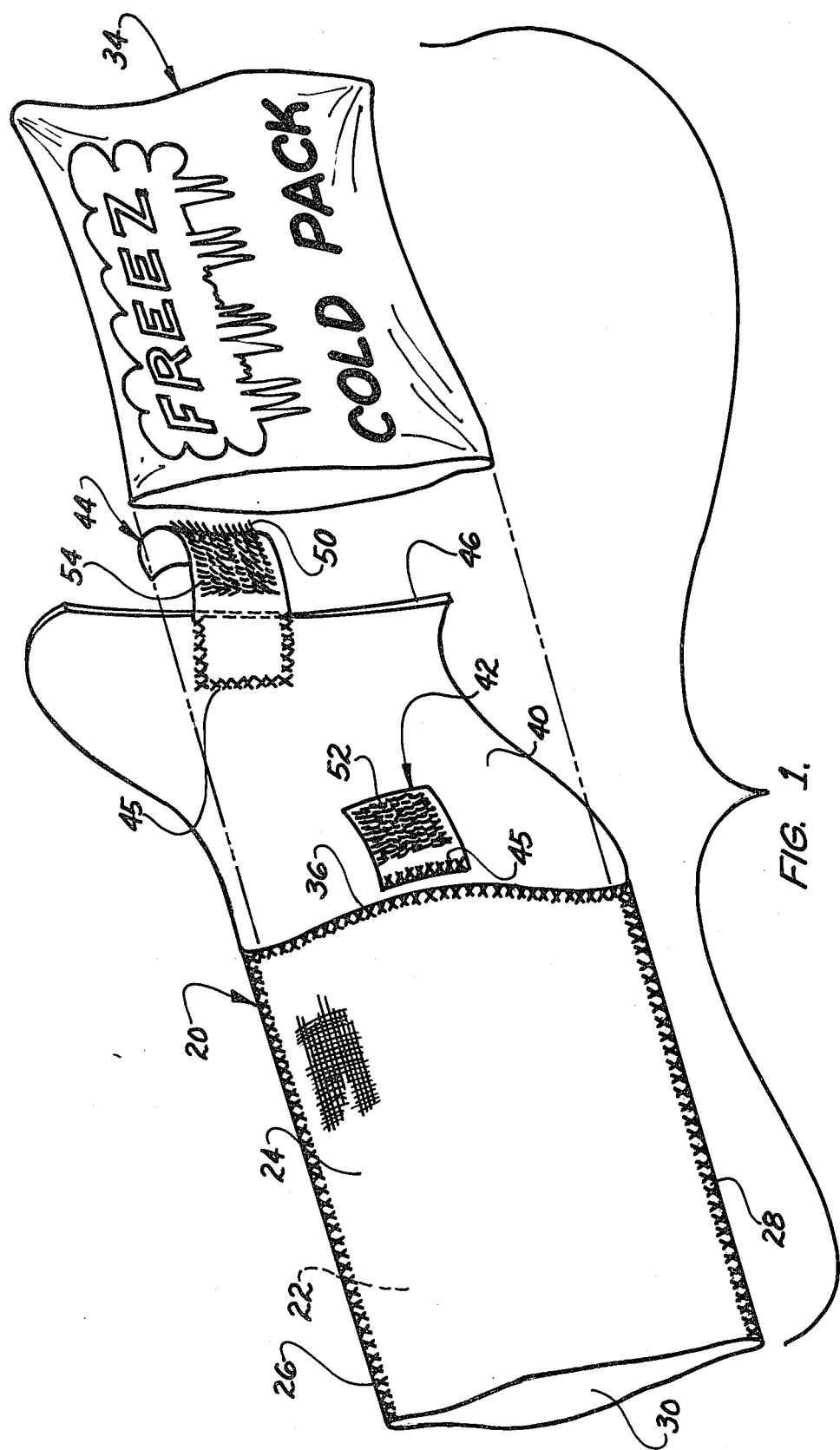
FIG. 1 is a perspective view of a cover for an instant cold pack constructed in accordance with the present invention.

Referring in detail to the drawings, FIG. 1 illustrates a cover 20 constructed in accordance with the present invention which cover includes first and second coextensive flexible sheet portions 22 and 24 joined together at side edges 26 and 28 and closed end edge 30 to form a pouch 32 for receiving an instant cold pack indicated generally at 34 in FIG. 1.

The right end edge 36 of second sheet portion 24 is normally unsecured with respect to first sheet portion 22 to provide an open end for pouch 32.

A third flexible sheet portion 40 is preferably formed by an extension of first sheet portion 22 and includes a faster means adapted for detachable engagement with the other sheet portions. Such fastener means comprises a first fastener element 42 mounted adjacent the open end of the pouch, so as to secure the first and second sheet portions 22 and 24 together at end edge 36 and therefore form a closure for the open end of the pouch after cold pack 34 has been inserted therein.

The fastener means also comprises a second fastener element 44 mounted on third sheet portion 40 at the extended edge 46 thereof, with such second fastener element being adapted for detachable engagement with the flexible sheet portions at various locations on the surface thereof.

Referring in detail to the two fastener elements 42 and 44, each is formed as a tab of flexible fabric that is sewn at seam 45 to third sheet portion 40 and includes a multiplicity of minute upstanding male protrusions 50 that extend upwardly from the surfaces 52 and 54 of both fastener elements 42 and 44.

It should now be mentioned that it has been determined, that the above described fastener elements will detachably engage with the surfaces of the flexible sheet portions at any selected locations thereon, if such sheet portions are formed of a specific material known as a nylon pile laminate which consists of nylon fabric manufactured of minute hair-like filaments that extend upwardly from the surface of the nylon fabric.

It has further been determined that if fastener elements 42 and 44 are fabricated from the male portion of a material known as Velcro tape, then these elements will firmly attach to any portion of the outer surfaces of flexible sheets 22 and 24 and 40 when the sheets are fabricated from the above mentioned nylon pile laminate.

With reference to instant cold pack 34, it will be understood that these items need not be refrigerated, as they consist of an outer sealed plastic envelope containing ammonium nitrate crystals and an inner ruptureable plastic envelope containing a solution, such as water with calcium chloride. When the outer envelope is squeezed, the inner solution package is easily ruptured, thereby mixing the contents, which rapidly cools the pack.

In operation, it will now be understood that the cover of the present invention is adapted for selective use in a plurality of emergency applications. For example, the cover can be used as a means for securing a cold pack to an injured limb. In such application, the cold pack is inserted in the pouch portion and fastening element 42 is secured to second sheet portion 24 by folding it over the open end of the pouch at end edge 36. The cover is next extended around the limb with the cold pack 34 overlying the injured area, and with fastener element 44 overlying the surface first sheet portion 22 at some appropiate location thereon, such that the cover and pack assembly properly fits the size and configuration of the particular limb. The fastener 44 is then attached with finger pressure. The cover and pack are then retained in position on the limb, and at the same time pack 34 is prevented from shifting away from the injured area, since the pack is fixed relative to the cover 20 by the pouch closing function of fastening element 42.

As another example, the cover of the present invention can be used merely as a cover for application of a hot or cold pack to areas of the body, such as the face, where a light weight none adhering hot or cold application is required. In such applications the third sheet portion 40 is merely folded down along edge 36 overlying relationship with second sheet portion 24 with the two fastener elements 42 and 44 being secured to the pile on sheet portion 24.

In any of the selected applications, the instant pack can readily be replaced when expired merely by detaching the fastener elements from the pile.

What is claimed is:

1. A flexible pack which can be positioned and held in place on a selected portion of the body, said pack including an open pouch having a flap which includes a first fastener and winds over and closes the opening of the pouch and an end portion having a separate second fastening means to removably attach said flap to the back surface of said pouch and forming a space between said pouch and said flap for receiving said portion of said body and to provide proper pressure thereon, said pouch being capable of receiving a cold-producing packet actuable by external pressure.

2. The pack of claim 1 in combination with said cold-producing packet, wherein the flap is wound around a limb of the body.

3. The flexible pack of claim 1 wherein the front surface of said flap has nylon grippers and the surface of said pouch is attachable to said grippers.

4. The flexible pack of claim 2 wherein the front surface of said flap has nylon grippers and the surface of said pouch is attachable to said grippers.

5. The flexible pack of claim 1 formed from a single sheet of material.

6. The flexible pack of claim 2 formed from a single sheet of material.

7. The flexible pack of claim 3 formed from a single sheet of material.

* * * * *